US008772340B2

(12) United States Patent
Artico et al.

(10) Patent No.: US 8,772,340 B2
(45) Date of Patent: Jul. 8, 2014

(54) PROCESS FOR THE PREPARATION OF FESOTERODINE OR A SALT THEREOF

(75) Inventors: Marco Artico, Parabiago (IT); Emanuele Attolino, Palagiano (IT); Pietro Allegrini, San Donato Milanese (IT); Gabriele Razzetti, Sesto San Giovanni (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 53 days.

(21) Appl. No.: 13/295,224

(22) Filed: Nov. 14, 2011

(65) Prior Publication Data

US 2012/0149772 A1 Jun. 14, 2012

(30) Foreign Application Priority Data

Dec. 9, 2010 (IT) .............................. MI2010A2262

(51) Int. Cl.
*A61K 31/216* (2006.01)
*A61K 31/225* (2006.01)
*C07C 69/34* (2006.01)

(52) U.S. Cl.
USPC ............ 514/546; 514/548; 560/129; 560/140

(58) Field of Classification Search
CPC . A61K 31/216; A61K 31/225; A61K 31/222; C07C 219/28; C07C 213/06
USPC ............................ 514/548, 546; 560/129, 140
See application file for complete search history.

(56) References Cited

U.S. PATENT DOCUMENTS

| 6,713,464 B1 | 3/2004 | Meese et al. |
| 6,858,650 B1 | 2/2005 | Meese et al. |
| 2003/0199582 A1 | 10/2003 | Hawley |

FOREIGN PATENT DOCUMENTS

| DE | WO 2007/144097 A1 | * | 12/2007 |
| EP | 0 957 073 A1 | | 11/1999 |
| EP | 1927585 A2 | | 6/2008 |
| EP | 2281801 A1 | | 2/2011 |
| WO | 94/11337 A1 | | 5/1994 |
| WO | 01/96279 A1 | | 12/2001 |
| WO | 2007/138440 A1 | | 12/2007 |
| WO | 2007/144091 A1 | | 12/2007 |
| WO | 2007140986 A1 | | 12/2007 |
| WO | WO 2009122303 A2 | * | 10/2009 |
| WO | 2010/010464 A2 | | 1/2010 |
| WO | 2007/147547 A1 | | 9/2011 |

OTHER PUBLICATIONS

Trisha A. Duffey, James A. MacKay, and Edwin Vedejs, Catalytic Parallel Kinetic Resolution under Homogeneous Conditions, J. Org. Chem. 2010, 75, 4674-4685; see particularly Table 1, p. 4676.*
De Castro et al., "Selective Nosylation of 1-Phenylpropane-1,3-diol and Perchloric Acid Mediated Friedel-Crafts Alkylation: Key Steps for the New and Straightforward Synthesis of Tolterodine", Synthesis, 2008, No. 12, pp. 1841-1844.
U.S. Appl. No. 12/914,316, filed Oct. 28, 2010.
U.S. Appl. No. 12/972,573, filed Dec. 20, 2010.

* cited by examiner

*Primary Examiner* — Kendra D Carter
*Assistant Examiner* — Jason A Deck
(74) *Attorney, Agent, or Firm* — Rothwell, Figg, Ernst & Manbeck, P.C.

(57) ABSTRACT

A process for the preparation of (R)-2-(3-diisopropylamino-1-phenylpropyl)-4-(hydroxymethyl)-phenol isobutyrate (Fesoterodine) or a pharmaceutically acceptable salt thereof having low content in impurities.

10 Claims, No Drawings

1

PROCESS FOR THE PREPARATION OF FESOTERODINE OR A SALT THEREOF

FIELD OF THE INVENTION

The present invention relates to a process for the preparation of (R)-2-(3-diisopropylamino-1-phenylpropyl)-4-(hydroxymethyl)-phenol isobutyrate (Fesoterodine) or a pharmaceutically acceptable salt thereof, having low content in impurities.

TECHNOLOGICAL BACKGROUND

Great efforts have been dedicated to the preparation of pharmaceuticals having minimum amounts of impurities. The control of impurities is a key parameter to evaluate the efficiency of a process and a huge number of variables have to be taken into account in order to select the reaction conditions and the control protocols necessary to ensure that marketed medicaments are pure and therefore safe.

The guidelines of the regulatory organizations, for example the Food and Drug Administration (FDA) of the United States, suggest that any impurities in the medicaments be identified, when present in amounts above 0.1% (i.e. 1.000 ppm).

It should be noticed that ppm means parts per million, therefore 1% corresponds to 10,000 ppm; 0.1 corresponds to 1,000 ppm; 0.01 corresponds to 100 ppm and 0.001 corresponds to 10 ppm.

Fesoterodine, namely (R)-2-(3-diisopropylamino-1-phenylpropyl)-4-(hydroxymethyl)-phenol isobutyrate, of formula (I)

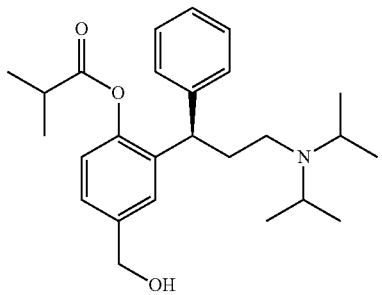

(I)

is a compound with antimuscarinic activity, used in clinics in the form of the fumarate salt for the treatment of the overactive bladder syndrome and in particular of urinary incontinence.

U.S. Pat. No. 6,713,464 discloses the preparation of Fesoterodine through different synthetic methods, inter alia according to the Scheme reported below.

Scheme

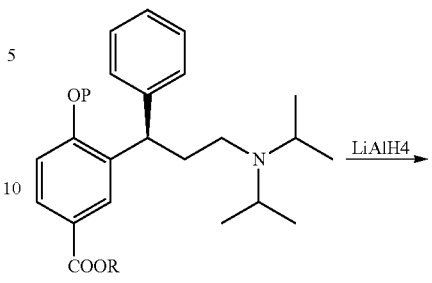

(A)

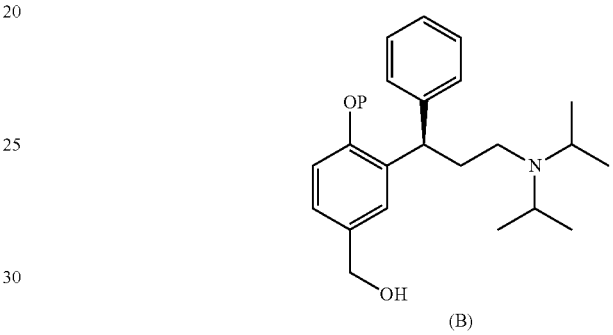

(B)

wherein P is a protecting group and R is hydrogen or alkyl.

Some of the known methods use as key intermediate a compound of formula (A), wherein R is hydrogen or methyl and P is a protective group for the phenolic hydroxyl, for example benzyl. Reduction with lithium aluminium hydride ($LiAlH_4$) of the carboxylic function of a compound of formula (A) provides a compound of formula (B), which can optionally be protected at the phenolic hydroxyl, and, if the case after deprotection, by selective esterification affords Fesoterodine of formula (I).

However, it should be noticed that the acylation reaction of the phenolic hydroxyl of a compound of formula (II) when carried out according to known techniques such as in U.S. Pat. No. 6,713,464, is not sufficiently regioselective, due to the presence of the primary hydroxyl group in the intermediate of formula (II).

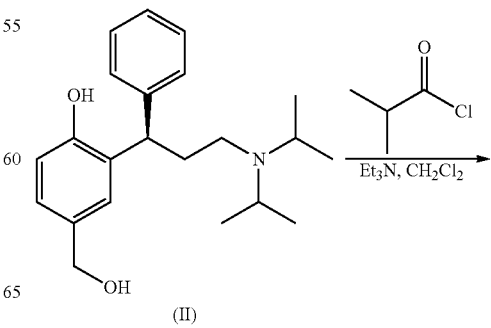

(II)

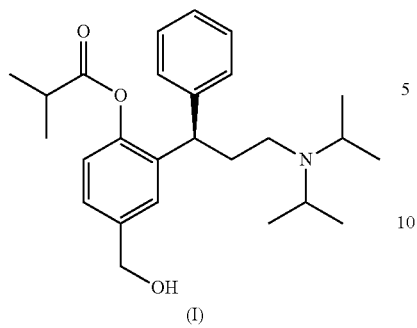

(I)

The low regioselectivity of the acylation reaction involves the formation of a compound of formula (III), a Fesoterodine regioisomer,

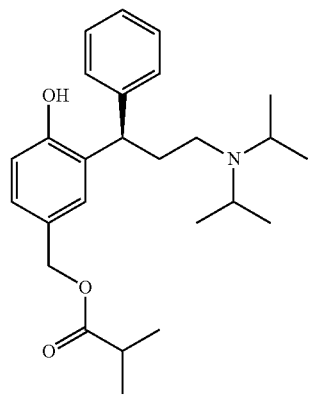

(III)

and of the diacylated compound of formula (IV)

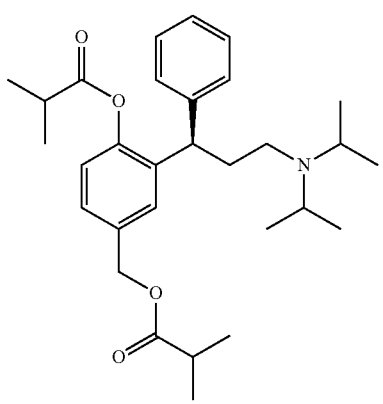

(IV)

These compounds and the process for the preparation thereof are known from U.S. Pat. No. 6,713,464.

The Applicant, using the acylation conditions already known, detected a further unknown impurity in the reaction crude, whose structure was found to correspond to compound of formula (V) by HPLC-MS and NMR.

(V)

This impurity proved particularly difficult to separate from Fesoterodine, even after conversion thereof to a crystallizable salt.

There is therefore the need for an alternative regio- and chemoselective esterification method which provides Fesoterodine or a pharmaceutically acceptable salt thereof, endowed with high regio- and chemoselectivity, and a low content in the impurities of formula (III) and/or (IV) and/or (V).

SUMMARY OF THE INVENTION

It was surprisingly found a process which overcomes the problems mentioned above and provides Fesoterodine, or a pharmaceutically acceptable salt thereof, having a very low content in impurities.

DETAILED DISCLOSURE OF THE INVENTION

Object of the invention is a process for the preparation of Fesoterodine of formula (I), or a pharmaceutically acceptable salt thereof

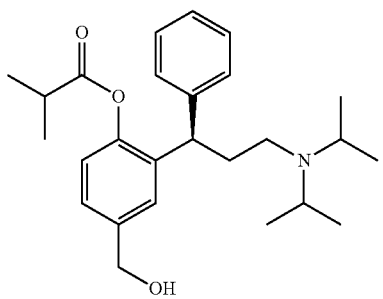

(I)

comprising the selective esterification of the phenolic hydroxyl of a compound of formula (II)

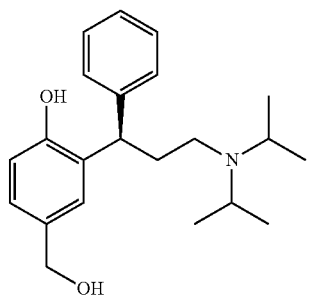

(II)

and, if desired, the conversion of a resulting compound of formula (I) to a pharmaceutically acceptable salt thereof, wherein the selective esterification comprises the reaction between the compound of formula (II) and an acylating agent in the presence of an alcoholic solvent and a base.

Pharmaceutically acceptable salts of a compound of formula (I), comprise for example fumarate, citrate, hydrochloride and sulfate, preferably fumarate and sulfate.

An acylating agent can be for example an isobutyryl halide, preferably isobutyryl chloride; or isobutyric anhydride.

An alcoholic solvent, as herein defined, can be for example a straight or branched $C_1$-$C_5$ alkanol, for example methanol, ethanol or isopropanol, preferably ethanol or a mixture of a $C_1$-$C_5$ alkanol with an inert solvent.

An inert solvent, as herein defined, is a solvent which does not react under the reaction conditions.

An inert solvent according to the present invention can be an aprotic polar solvents, such as dimethylformamide, dimethylacetamide, N-methylpyrrolidone, dimethylsulfoxide, acetonitrile; a $C_3$-$C_8$ ketone, preferably methyl isobutyl ketone; a cyclic or acyclic ether, typically tetrahydrofuran and methyl-tertbutil ether; an ester, typically ethyl acetate, isopropyl acetate, butyl acetate; a chlorinated solvent, typically dichloromethane; or an aromatic hydrocarbon, typically toluene; or a mixture thereof.

An alcoholic solvent as a mixture with an inert solvent is preferably an ethanol-toluene, dichloromethane-ethanol, ethanol-methanol or ethanol-tetrahydrofuran mixture.

A base, as herein defined, can be organic or inorganic; an organic base can be for example a tertiary amine, such as triethylamine, diisopropylethylamine or N-methyl-morpholine; preferably triethylamine or N-methylmorpholine. A strong or weak inorganic base, is typically a hydroxide, carbonate, bicarbonate, phosphate, mono or dihydrogen phosphate of an alkali or alkaline-earth metal, preferably sodium or potassium. An inorganic base is preferably potassium carbonate or sodium hydroxide.

The amount of base used is typically at least stoichiometric to the compound of formula (II).

After completion of the acylation reaction, the reaction mixture can undergo conventional acid-base aqueous treatments, known to those skilled in art, in order to isolate Fesoterodine as the free base or as a pharmaceutically acceptable salt thereof.

The conversion of a compound of formula (I) to a pharmaceutically acceptable salt thereof can be carried out by known methods, for example by treating the compound of formula (I) with an organic or inorganic acid aqueous solution.

A compound of formula (II) can be obtained by chemoselective reduction of the carboxylate group of a compound of formula (VIa)

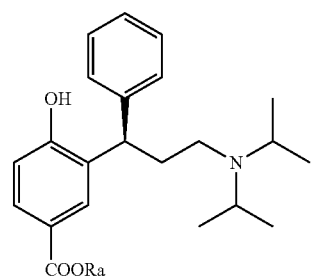

(VIa)

wherein Ra is straight or branched $C_1$-$C_6$ alkyl, according to known methods.

A compound of formula (VIa), or a salt thereof, can be for example prepared by a process comprising the reaction between a compound (VII)

(VII)

wherein Ra is as defined above, and a compound of formula (VIII)

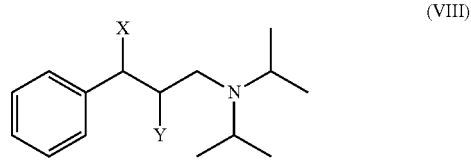

(VIII)

wherein X is a group capable of generating a benzyl carbocation and Y is hydrogen, or X and Y, taken together, form a double bond;

in the presence of a strong acid, to obtain a compound of formula (VI)

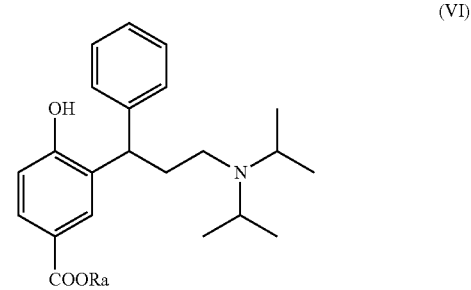

(VI)

and its subsequent resolution via formation of a diastereomeric salt with an optically active organic acid.

Examples of group X capable of generating a benzyl carbocation are a hydroxy group or a reactive derivative thereof, such as a $C_1$-$C_6$ alkyl ether or aryl ether, a $C_1$-$C_6$ alkylcarboxylate or arylcarboxylate, a $C_1$-$C_6$ alkylsulfonate or arylsulfonate, a trifluoromethanesulfonate, a sulfate, nitrate, phosphate; or a halogen, for example chlorine, bromine or iodine.

A strong acid, as herein defined, can be a strong protic acid, such as hydrochloric, sulfuric, hydrobromic, perchloric, polyphosphoric, trifluoroacetic, methanesulfonic, p-toluenesulfonic and trifluoromethanesulfonic acid, preferably methanesulfonic acid or a Lewis acid such as $AlCl_3$, $FeCl_3$ and $BF_3$ etherate.

Preferably, when X is a hydroxy group or a $C_1$-$C_6$ alkyl ether or aryl ether and Y is hydrogen, or when X and Y, taken together, form a double bond, the strong acid is preferably protic; whereas when X is a halogen atom and Y is hydrogen, the strong acid is preferably a Lewis acid.

An optically active organic acid can be an optically active carboxylic or sulfonic acid.

An optically active carboxylic acid can be selected from e.g. (+) or (−) tartaric acid, (+) or (−) 2,3-dibenzoyl-tartaric acid, mandelic acid, 3-chloro mandelic acid and abietic acid; a sulfonic acid is for example S-(+)-camphorsulfonic acid.

Following an analogous process to that described above, starting from the (S) enantiomer of a compound of formula (II), which can be obtained by chemoselective reduction of the carboxylate group of the (S) enantiomer of a compound of formula (VIa), the (S) enantiomer of a compound of formula (I), i.e. (S)-Fesoterodine, can be obtained.

Fesoterodine of formula (I), or a resulting salt thereof, has a content in a compound of formula (III) and/or (IV) and/or (V) ranging from 0.0001% to about 0.1%, for each of them.

A further object of the present invention is therefore a process for the preparation of a compound of formula (I) or a pharmaceutically acceptable salt thereof, according to the process disclosed above, containing an amount of a compound of formula (III) and/or (IV) and/or (V)

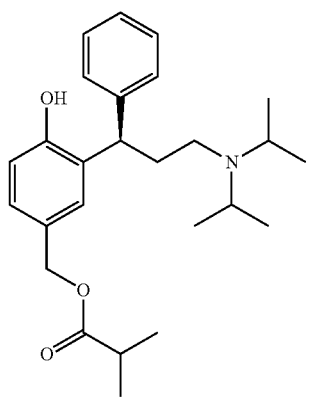

(III)

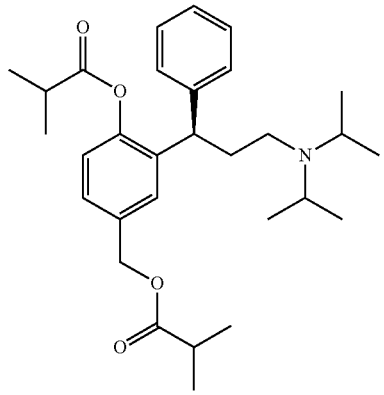

(IV)

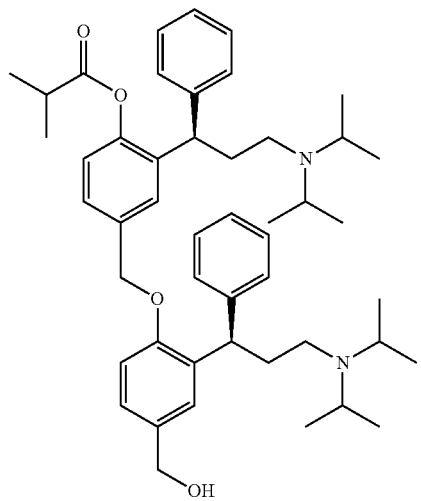

(V)

comprised between about 0.0001% to about 0.1%, for each of them.

A further object of the present invention is a pharmaceutical composition comprising a compound of formula (I), or a pharmaceutically acceptable salt thereof, and a compound of formula (III) and/or (IV) and/or (V) in amounts typically ranging from 0.0001% to 0.1%, for each of them, and a pharmaceutically acceptable excipient and/or carrier.

The pharmaceutical composition of the invention can be prepared according to known methods in pharmaceutical technique in different forms, such as tablets, powders, lozenges, capsules, syrups, injectable solutions and controlled release pharmaceutical formulations. Examples of excipients can be ligands, disintegrants, diluents, suspending agents, emulsifiers and flavours. The dosage for the administration to a mammal, including man, is typically the same as used in clinics for Fesoterodine. Anyway, the choice of the dosage is left to the discretion of the physician.

The amount of each impurity of formula (III) and/or (IV) and/or (V) as defined above, in a mixture comprising a compound of formula (I), and one or more of said impurities of formula (III) and/or (IV) and/or (V), can be determined using the conventional analytic techniques known to those skilled in the art.

By way of example, impurities of formula (III) and/or (IV) and/or (V) can be detected by normal or reverse phase HPLC. The evaluation of the content of impurities of formula (III) and/or (IV) and/or (V) is of paramount importance, particularly in a process for the preparation of Fesoterodine or a pharmaceutically acceptable salt thereof, as it affects the industrial applicability of the process itself.

Therefore a further object of the present invention is the use of a compound of formula (III) and/or (IV) and/or (V) as defined above, as analytical standard. In particular, a compound of formula (III) and/or (IV) and/or (V) can be used as analytical standard in a process for the preparation of Fesoterodine of formula (I), or a pharmaceutically acceptable salt thereof.

A further object of the present invention is therefore a process for the preparation of Fesoterodine of formula (I), or a pharmaceutically acceptable salt thereof according to the process described above, comprising the use of a compound of formula (III) and/or (IV) and/or (V) as analytical standard.

The compound of formula (V) is novel and is a further object of the present invention.

Such compound can be isolated by flash chromatography on silica gel (ethyl acetate/methanol/ammonia) from the acylation crudes obtained according to what reported in U.S. Pat. No. 6,713,464.

The following examples illustrate the invention.

Example 1

Synthesis of R-(+)-2-(3-diisopropylamino-1-phenyl-propyl)-4-hydroxymethyl-phenyl isobutyrate (Fesoterodine)

A 2 l glass reactor, equipped with mechanical stirrer, thermometer, cooler and under nitrogen, is loaded with 85 g of compound of formula (II) (0.249 mols) dissolved in 135 ml of ethanol and 510 ml of toluene. The solution is cooled to about 0° C. under stirring, then treated with solid potassium carbonate (68.8 g, 0.498 mols) portionwise. After completion of the addition, 37 g (0.347 mols) of isobutyryl chloride is slowly dropped into the suspension and the reaction is monitored by HPLC. Upon completion of the reaction, the mixture is diluted with water (about 300 ml) and the temperature of the biphasic mixture is adjusted to about 20° C. The phases are separated, then the organic phase is washed with an acetic acid diluted solution. The phases are separated and the aqueous phase is re-adjusted to basic pH (about 9-10) by addition of dilute sodium hydroxide, then extracted with methyl tert-butyl ether. The organic phase is evaporated under reduced pressure to obtain Fesoterodine base as a thick, oily residue (about 98 g) in 96% yield, with HPLC purity higher than 99% and a content of each of the impurities (III), (IV), and (V) lower than 0.1% by area calculated by HPLC.

$^1$H-NMR (300 MHz, CDCl$_3$, 28° C.): δ 7.34 (d, 1H); 7.28-7.12 (m, 6H); 4.62 (s, 2H); 4.12 (t, 1H); 2.98 (m, 2H); 2.80 (m, 1H); 2.34 (m, 2H); 2.14 (m, 2H); 1.32 (dd, 6H); 0.92 (dd, 12H).

Example 2

Synthesis of R-(+)-2-(3-diisopropylamino-1-phenyl-propyl)-4-hydroxymethyl-phenyl isobutyrate (Fesoterodine)

A 250 ml glass reactor, equipped with magnetic stirrer, cooler and under nitrogen, is loaded with 7.14 g of compound of formula (II) (21 mmoles) dissolved in 63 ml of dichloromethane and 7 ml of ethanol. The solution is cooled to about 0° C. under stirring, then treated with solid potassium carbonate (2.90 g, 27 mmoles). After completion of the addition, 2.9 g (21 mmoles) of isobutyryl chloride is slowly dropped into the suspension in about 15 minutes at room temperature and the reaction is monitored by HPLC. Upon completion of the reaction, the mixture is diluted with water (about 30 ml) and the temperature of the biphasic mixture is adjusted to about 20° C. The phases are separated, then the organic phase is washed with an acetic acid diluted solution. The phases are separated and the aqueous phase is re-adjusted to basic pH (about 9-10) by addition of potassium carbonate, then extracted with dichloromethane. The organic phase is dried, filtered and then evaporated under reduced pressure to obtain Fesoterodine base as a thick, oily residue in 95.3% yield, with HPLC purity higher than 99%.

$^1$H-NMR (300 MHz, CDCl$_3$, 28° C.): δ 7.34 (d, 1H); 7.28-7.12 (m, 6H); 4.62 (s, 2H); 4.12 (t, 1H); 2.98 (m, 2H); 2.80 (m, 1H); 2.34 (m, 2H); 2.14 (m, 2H); 1.32 (dd, 6H); 0.92 (dd, 12H).

Example 3

Synthesis of R-(+)-2-(3-diisopropylamino-1-phenyl-propyl)-4-hydroxymethyl-phenyl isobutyrate (Fesoterodine)

A 100 ml one-necked glass reactor, equipped with magnetic stirrer, cooler and under nitrogen, is loaded with 2 g of compound of formula (II) (5.87 mmoles) dissolved in 18 ml of dichloromethane and 2 ml of ethanol. The solution is cooled to about 0° C. under stirring, then treated with triethylamine (1.64 mL; 11.74 mmoles). After completion of the addition, 750 mg of isobutyryl chloride is added dropwise at room temperature and the reaction is monitored by HPLC. Upon completion of the reaction, the mixture is diluted with water (about 10 ml) and the temperature of the biphasic mixture is readjusted to about 20° C. The phases are separated, the organic phase is then washed with an acetic acid diluted solution. The phases are separated and the aqueous phase is re-adjusted to basic pH (about 9-10), then extracted with dichloromethane. The organic phase is dried, filtered and then evaporated under reduced pressure to obtain Fesoterodine base as a thick, oily residue in 89.6% yield and HPLC purity higher than 99%.

$^1$H-NMR (300 MHz, CDCl$_3$, 28° C.): δ 7.34 (d, 1H); 7.28-7.12 (m, 6H); 4.62 (s, 2H); 4.12 (t, 1H); 2.98 (m, 2H); 2.80 (m, 1H); 2.34 (m, 2H); 2.14 (m, 2H); 1.32 (dd, 6H); 0.92 (dd, 12H).

Examples 4-6

Synthesis of R-(+)-2-(3-diisopropylamino-1-phenyl-propyl)-4-hydroxymethyl-phenyl isobutyrate (Fesoterodine)

By proceeding analogously to the procedure of Example 3, the compound of formula (II) (2 g, 5.87 mmoles) is reacted in the following alcoholic solvent/base mixtures, and the following results are obtained:

| Ex no. | Acylating agent, equivalents | Solvent | Base, equivalents | Fesoterodine (yield %) |
| --- | --- | --- | --- | --- |
| 4 | Isobutyryl chloride, 2 | Dichloromethane/ethanol 10:1 (40 mL/4 mL) | N-methyl-morpholine, 2 | 93.7% |
| 5 | Isobutyryl chloride, 2 | Ethanol/Methanol (8 mL/1 mL) | NaOH, 1 | 92.3% |
| 6 | Isobutyric anhydride, 2 | Ethanol/Tetrahydrofuran | Potassium carbonate, 2 | 83.8% |

Fesoterodine base obtained according to Examples 4-6 has HPLC purity higher than 99%.

The invention claimed is:

1. A process for the preparation of Fesoterodine of formula (I), or a pharmaceutically acceptable salt thereof

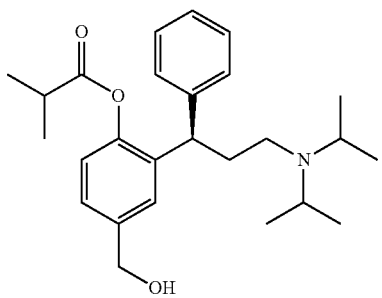
(I)

comprising the selective esterification of the phenolic hydroxyl of a compound of formula (II)

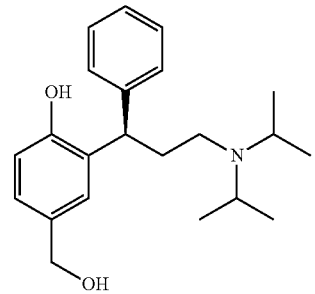
(II)

wherein the selective esterification comprises the reaction of a compound of formula (II) with an acylating agent, in the presence of an alcoholic solvent and a base, wherein said alcoholic solvent is a $C_1$-$C_2$ alkanol, a mixture of $C_1$-$C_2$ alkanols or a mixture of a $C_1$-$C_2$ alkanol with an inert solvent.

2. The process according to claim 1 wherein the acylating agent is an isobutyryl halide or isobutyric anhydride.

3. The process according to claim 1 wherein the inert solvent is selected from the group consisting of a polar aprotic solvent, a $C_3$-$C_8$ ketone, a cyclic or acyclic ether, an ester, a chlorinated solvent, an aromatic hydrocarbon and a mixture thereof.

4. The process according to claim 1 wherein the alcoholic solvent is an ethanol-toluene, dichloromethane-ethanol, ethanol-methanol or ethanol-tetrahydrofuran mixture.

5. The process according to claim 1 wherein the base is an organic or inorganic base selected from the group consisting of a tertiary amine, a hydroxide, carbonate, bicarbonate, phosphate, and a monophosphate or dihydrogen phosphate of an alkali metal or alkali earth metal.

6. The process according to claim 1 wherein the base is potassium carbonate or sodium hydroxide.

7. The process according to claim 1 wherein the base is triethylamine or N-methyl-morpholine.

8. The process according to claim 1 wherein the amount of base is at least stoichiometric to the compound of formula (II).

9. A process for the preparation of a composition comprising a compound of formula (I) or a pharmaceutically acceptable salt thereof,

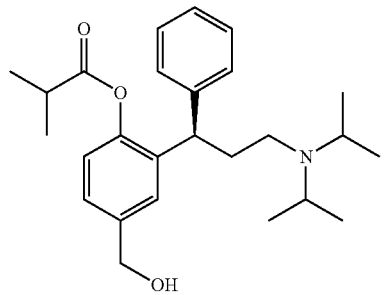
(I)

wherein said composition comprises at least one compound with a formula selected from the group consisting of formula (III), formula (IV) and formula (V)

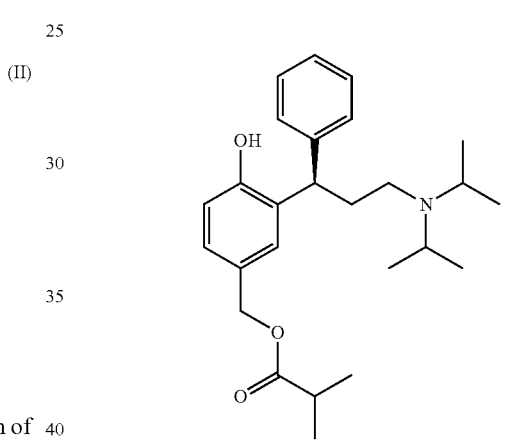
(III)

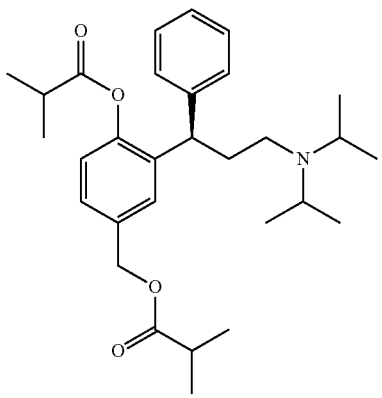
(IV)

-continued

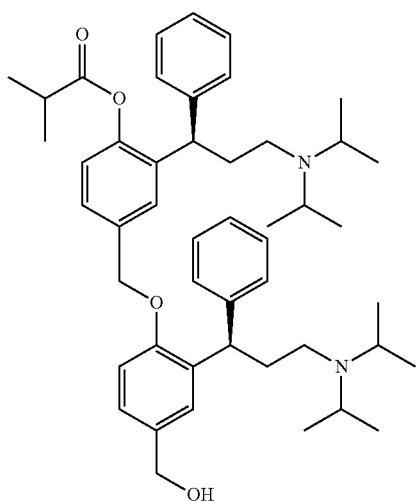
(V)

in an amount between about 0.0001% to about 0.1%, wherein said compound of formula (I) is prepared by a process comprising the selective esterification of the phenolic hydroxyl of a compound of formula (II)

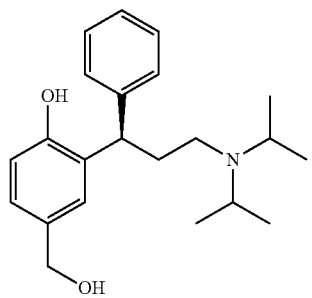
(II)

wherein the selective esterification comprises the reaction of a compound of formula (II) with an acylating agent, in the presence of an alcoholic solvent and a base, wherein said alcoholic solvent is a $C_1$-$C_2$ alkanol, a mixture of $C_1$-$C_2$ alkanols or a mixture of a $C_1$-$C_2$ alkanol with an inert solvent.

10. The process according to claim 1, further comprising converting the resulting compound of formula (I) to a pharmaceutically acceptable salt thereof.

* * * * *